(12) United States Patent
Lechot

(10) Patent No.: US 6,264,647 B1
(45) Date of Patent: Jul. 24, 2001

(54) INSTRUMENT HOLDER FOR SURGICAL INSTRUMENT

(75) Inventor: André Lechot, Orvin (CH)

(73) Assignee: Precifar S.A., Orvin (CH)

(*) Notice: Subject to any disclaimer, the term of this patent is extended or adjusted under 35 U.S.C. 154(b) by 0 days.

(21) Appl. No.: 09/602,341

(22) Filed: Jun. 24, 2000

(30) Foreign Application Priority Data

Mar. 2, 2000 (CH) ...................................................... 409/00

(51) Int. Cl.7 .................................................. A61B 17/00
(52) U.S. Cl. .......................................................... 606/1
(58) Field of Search ...................................................... 606/1

(56) References Cited

U.S. PATENT DOCUMENTS

| 5,236,433 | 8/1993 | Salyer . | |
|---|---|---|---|
| 5,582,607 | * 12/1996 | Lackman | 606/1 |
| 5,658,290 | 8/1997 | Lechot . | |
| 6,093,184 | * 7/2000 | Campbell et al. | 606/1 |

* cited by examiner

*Primary Examiner*—Linda C. M. Dvorak
*Assistant Examiner*—Jocelyn Debra Ram
(74) *Attorney, Agent, or Firm*—Bugnion S.A.; John Moetteli

(57) ABSTRACT

Instrument holder comprising a shank (1) equipped with a head (2) designed to receive an instrument and a locking component (4) pushed against the head by a spring (9) bearing on a ring (11) sliding on the shank, and having means of connection (8, 12) on the shank which is engaged by rotation of the ring, in such a way that the release of the ring allows the locking component, the spring and the ring to slide freely in order to permit cleaning of the instrument holder.

2 Claims, 1 Drawing Sheet

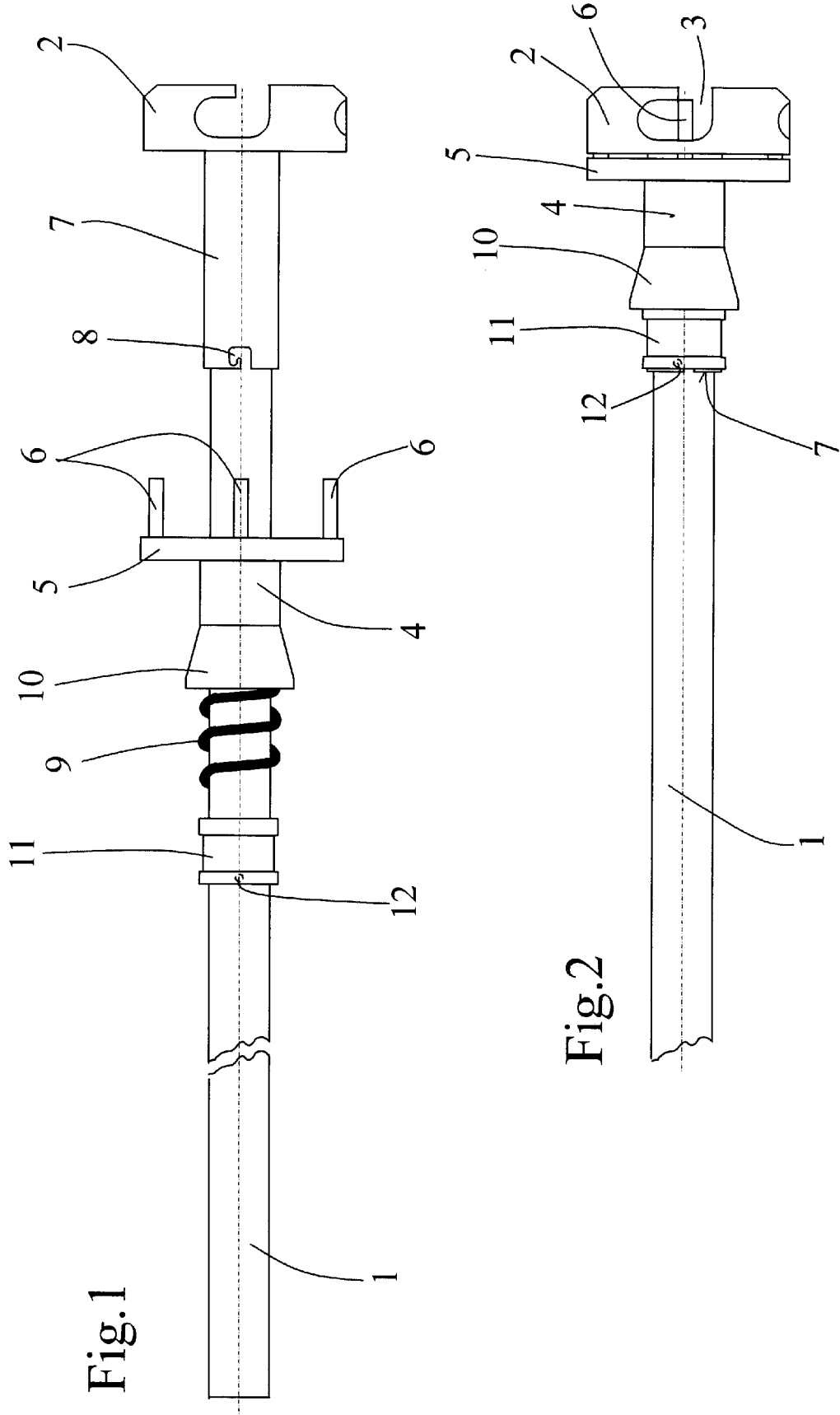

INSTRUMENT HOLDER FOR SURGICAL INSTRUMENT

BACKGROUND OF THE INVENTION

The invention relates to an instrument holder for a surgical instrument, comprising a shank equipped with a head designed to receive an instrument, and an annular locking component mounted so as to slide about the shank, under the head, equipped with locking means which cooperate with the head so as to lock the instrument on the head, and pushed against the head by a helical spring.

An instrument holder of this type is known in particular from U.S. Pat. No. 5,658,290 and U.S. Pat. No. 5,236,433, the contents of which are incorporated by reference.

A surgical instrument, for example for preparing for the fitting of a hip prosthesis, works in a medium which causes considerable soiling of the instrument and the instrument holder. Moreover, a surgical instrument holder must be cleaned very frequently and very carefully in order to avoid any risk of infection. However, cleaning of surgical instruments is difficult, in particular cleaning of the space between the shank and the locking component on account of the presence of bone debris and coagulated blood.

SUMMARY OF THE INVENTION

The object of the invention is to provide optimum conditions for rapid cleaning.

To this end, the instrument holder according to the invention is distinguished by the fact that the thrust spring bears on a ring sliding on the shank, and that the shank and the ring have means of connection set in use manually by rotation of the ring, in such a way that the release of the ring allows the locking component, the spring and the ring to slide freely on the shank. This almost instantaneous disassembly of the component parts of the instrument holder allows it to be thoroughly and quickly cleaned.

According to a preferred embodiment of the invention, the shank has, under the head, a section with a diameter greater than the diameter of the rest of the shank, on which section the ring is fixed by a bayonet fastening.

The play of the components making up the locking means on the shank permits good cleaning without it being necessary to remove these components from the shank, which avoids the risk of losing a component or mixing them up, and it obviates the need to fit the components back on the shank. The fastening and release of the ring take place instantaneously, which represents a saving in time. This makes it possible to ensure that a complete kit of instruments is not rendered unusable because of a single component being inoperative.

The head and the fastening and locking means of the instrument can be designed in many ways. These means do not form part of the actual invention.

BRIEF DESCRIPTION OF THE DRAWINGS

The attached drawing shows an embodiment of the invention by way of example.

FIG. 1 shows the instrument holder in the disassembled position.

FIG. 2 shows the instrument holder in the locked position.

DETAILED DESCRIPTION OF THE PREFERRED EMBODIMENT(S)

The instrument holder shown comprises a cylindrical shank 1 at one end of which a head 2 is fixed which is identical to the head described in U.S. Pat. No. 5,658,290, the content of which is incorporated by reference. This head has a central recess, the head forming a crown around this recess. This crown has four bayonet catches 3 diametrically opposite in pairs. A reamer analogous to the reamer shown and described in U.S. Pat. No. 5,658,290 is fixed in these catches 3. The reamer is locked in the catches 3 by an annular locking component 4 equipped with a plate 5 having four parallel fingers 6 which pass through the head 2 in order to close the bayonet catches 3, as is described in U.S. Pat. No. 5,658,290.

The locking component 4 does not slide directly on the section of the shank seen in FIG. 1, but on a section 7 with a greater diameter than the diameter of the rest of the shank. This section 7 can consist of a tubular component arranged on the shank 1. At least one bayonet catch 8 is formed at the end of the section 7 remote from the head 2. These catches are preferably at least two in number and diametrically opposed to facilitate assembly, as will be seen below. Also arranged around this section 7 there is a helical spring 9 which engages in a frustoconical widened part 10 of the locking component 4 and bears against this locking component, the median part of which slides freely on the section 7. The instrument holder is completed by a ring 11 which also slides on the section 7 and is equipped internally with a radial stud 12, that is oriented in the direction of the shank 1.

Starting from the disassembled position shown in FIG. 1, and in order to assemble the instrument holder, the locking component 4 is brought under the head 2, engaging its locking fingers 6 through the head, then, with the ring 11, the spring 9 is pushed against the locking component 4 and this spring is compressed, at the same time turning the ring 11 to the left until its stud 12 engages in the bayonet catch 8 respectively in one of the bayonet catches, in which it fastens by holding the ring 11 which is pushed rearward by the spring 9. The instrument holder can then be used as is described in U.S. Pat. No. 5,658,290. The frustoconical widened part 10 gives a grip for the thumb and index finger for pulling the locking component 4 back counter to the action of the spring 9 in order to release the instrument fixed on the instrument holder.

Conversely, in order to disassemble the instrument holder, it suffices to push the ring 11 forward counter to the action of the spring 9 and to turn it in the direction of the hands of a watch in such a way that its stud 12 is pushed out of the bayonet catch 8 by the spring 9.

It will be seen that assembly and disassembly of the instrument holder are effected instantaneously and can be done using one hand.

As is shown in FIG. 1, the shank 1 allows the components 4, 9 and 11 to be removed totally from the shank. Given the substantial play of the components 4 and 11 on the shank 1, such complete disassembly is not necessary for cleaning purposes. It i s therefore possible to provide an abutment at the end of the shank in order to hold the components on the shank.

The end of the shank remote from the head 2 is shown as being cylindrical, but it can have another shape, in particular a hexagonal cross section for fastening the instrument holder on the means for driving the instrument holder in rotation.

The ring 11 could be made integral with the shank by screwing, that is to say having a screw thread in the ring and on the part 7.

The head 2 and the fingers 6 are only one example from all the possible means for connection of an instrument.

Although illustrative embodiments of the invention have been shown and described a wide range of modification, change and substitution is contemplated in the foregoing disclosure and in some instances, some features of the present invention may be employed without a corresponding use of the other features. Accordingly it is appropriate that the appended claims be construed broadly and in a manner consistent with the scope of the invention.

What is claimed:

1. An instrument holder for a surgical instrument comprising a shank equipped with a head adapted to receive an instrument; an annular locking component mounted so as to slide along the shank, under the head, equipped with a locking means which cooperates with the head so as to lock the instrument on the head; wherein the locking component is pushed against the head by a helical spring, said spring bears on a ring which slides on the shank, and the shank and the ring have a connection means engaged in such a way that the release of the ring allows for disassembly.

2. The instrument holder as claimed in claim 1, wherein the shank has, under the head, a section with a diameter greater than the diameter of the rest of the shank, and the ring is fixed on said section of the shank by a bayonet fastening.

* * * * *